US00PP12485P2

(12) United States Plant Patent
Utecht

(10) Patent No.: US PP12,485 P2
(45) Date of Patent: Mar. 26, 2002

(54) GERANIUM PLANT NAMED 'FISORANGE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/632,245

(22) Filed: Aug. 3, 2000

(51) Int. Cl.[7] ..... A01H 5/00
(52) U.S. Cl. ..... Plt./327
(58) Field of Search ..... Plt./327, 328

(56) References Cited

U.S. PATENT DOCUMENTS

PP5,374 P * 12/1984 Schumann ..... Plt./328

OTHER PUBLICATIONS

GTITM UPOVROM citation for 'Fisorange' as per QZ PBR 980824; Jun. 15, 1998.*
Fischer Selections 1999/2000 Catalogue.
Swiss Application for 'Fisorange' (Apr. 22, 1999).
European Union Application for 'Fisorange' (Aug. 17, 1998).
European Union Grant for 'Fisorange' (Aug. 16, 1999).
German Application for 'Fisorange' (Aug. 15, 1997).
German Denomination for 'Fisorange' (Jul. 15, 1998).
German Grant for 'Fisorange' (Jan. 15, 1999).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisorange', as described and illustrated, and particularly characterized by the combined features of deep salmon-orange flower color, round, cup-like flower shape, fresh-green foliage with strong zonation, medium-tall, well-branched, round plant habit, moderately early spring flowering response and rich flowering throughout the summer.

1 Drawing Sheet

BACKGROUND OF THE INVENTION

The present invention relates to a new and distinct cultivar of geranium plant, botanically known as *Pelargonium zonale*, and hereinafter referred to by the cultivar name 'Fisorange'.

'Fisorange' is a product of a planned breeding program which had the objective of creating new geranium varieties with salmon-pink to deep salmon, semi-double flowers, zoned foliage and medium-tall plant habit.

'Fisorange' originated from a hybridization made by the inventor, Angelika Utecht, in a controlled breeding program in Galdar, Gran Canaria, Spain, in 1994. The female parent was the cultivar 'Fispera' (unpatented), which was characterized by orange-red, single-type flowers, dark-green foliage with distinct zonation, and medium-tall plant habit. The male parent was a hybrid seedling, designated no. 1232-1 (unpatented), characterized by orange-red, semi-double flowers, dark-green foliage with strong zonation and relatively compact plant habit.

'Fisorange' was selected as one flowering plant within the progeny of the stated cross by the inventor, Angelika Utecht, in 1995 in a controlled environment in Galdar, Gran Canaria, Spain.

The first act of asexual reproduction of 'Fisorange' was accomplished when vegetative cuttings were taken from the initial selection in autumn 1995 in a controlled environment in Galdar, Gran Canaria, Spain, by, or under the supervision of, Angelika Utecht. Horticultural examination of plants grown from these cuttings, initiated in May 1996 in Hillscheid, Germany, and continuing thereafter, has demonstrated that the combination of characteristics as herein disclosed for 'Fisorange' are firmly fixed and are retained through successive generations of asexual reproduction.

BRIEF DESCRIPTION OF THE INVENTION

The following traits have been repeatedly observed and are determined to be basic characteristics of 'Fisorange', which in combination distinguish this geranium as a new and distinct cultivar:

1. Intense salmon-orange, semi-double, cup-shaped flowers;
2. Relatively large, round umbels;
3. Medium-green foliage with strong zonation;
4. Fairly compact plant habit under greenhouse conditions;
5. Moderately vigorous, well-branched growth in outdoor environment; and
6. Early to medium spring flowering response, and rich flowering throughout the summer.

'Fisorange' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisorange' are the varieties 'Flomono' (unpatented), 'Schöne Helena' (U.S. Plant Pat. No. 5,374), 'Fisfid' (U.S. Plant Pat. No. 7,388), and 'Bergpalais' (unpatented). In comparison to 'Flomono', 'Fisorange' has a more intense orange flower color, smaller leaves with somewhat more distinct lobing and with stronger zonation, and somewhat taller plant habit.

In comparison to 'Schoene Helena' and 'Fisfid', 'Fisorange' has a more intense, more orange tone of flower color and distinctly stronger zonation. In comparison to 'Bergpalais', 'Fisorange' has a slightly more intense general flower color, smaller, more cup-shaped flowers than the flowers of 'Bergpalais' which open wider, somewhat more intense zonation of leaves, and wider plant habit.

BRIEF DESCRIPTION OF THE DRAWING

The accompanying photographic illustration shows typical flower and foliage characteristics of 'Fisorange' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium zonale* L'Hérit.

*Commercial.*—Zonal geranium, cv. 'Fisorange'.

Inflorescence:

*Umbel.*—Shape: Semi-spherical to spherical. Average diameter: 98 mm. Average depth: 55 mm. Peduncle length: 149 mm. Peduncle color: Light-green, from RHS 143 A to RHS 143 B. Pedicel length: 25 mm. Pedicel color: Middle and upper part is reddish, varying between RHS 179 A and RHS 179 B; base is green RHS 144 A. Number of flowers per umbel: Approximately 25–35. Lastingness of umbel: Approximately 20 days.

*Corolla.*—Average diameter: 42 mm. Form: Semi-double. Shape: Round, cup-shaped. Number of petals: 6.5. Size of petals: Upper petals are 25–27 long, 18–19 mm wide; lower petals are 23–25 mm long, 22–24 mm wide. Shape of petals: Obovate, attenuate base, upper end rounded, margin entire. Color (general tonality from a distance of three meters): Salmon-orange. Color of upper petals: Mainly RHS 40 B. Markings of upper petals: Weak, orange-red veins RHS 42 A. Color of lower petals: Mainly RHS 40 B, near margin possibly lighter, RHS 41 C. Color of lower surface of petals: Near RHS 41 C, slightly marbled. Number of petaloids: 0–2. Color of petaloids: Upper surface RHS 40 B, lower surface RHS 41 C, base RHS 15 D. Color of sepals: Outer surface green RHS 143 C, base RHS 179 A; inner surface light green RHS 144 A, base RHS 179 B. Number of sepals: 5. Size of sepals: 11–12 mm long, 4 mm wide for the largest upper sepal, 3 mm wide for other sepals. Shape of sepals: Linear to lanceolate, acute tip, base truncate, surface weak with pubescence, margin entire.

*Bud (just before petals unfold).*—Shape: Broad elliptical. Color (sepals): Light-green, RHS 143 A. Color (petals): Salmon-orange varying from RHS 41 A to RHS 41 C, marbled. Length: 13 mm. Width: 8 mm.

*Reproductive organs.*—Androecium: About 5 fertile anthers, with white filaments and orange pollen varying between RHS 30 A to RHS 33 A, plentiful quantity of pollen produced. Gynoecium: 5–6-lobed stigma, rose-red stigma and filament, one pistil per flower. Fertility/seed set: Slight seed set may occur, oblong shape, 4–5 mm long, brown RHS 177 B.

*Spring flowering response period.*—In Hillscheid, Germany, in 1999, plants had on average 0.9 flowers opened 8 weeks after planting of rooted cuttings.

*Outdoor flower production.*—Rich, the flower count in 1999, in Hillscheid, Germany, indicated about 4–5 inflorescences per plant in mid-May.

*Durability.*—Good shatter resistance, fair resistance fair and good stability of the flower color.

*Lastingness of individual bloom.*—Approximately 9 days at 18° C.

*Fragrance.*—None.

Plant:

*Foliage.*—Form: Kidney-shaped, open base. Apex: Rounded. Base: Open to wide open, cordate. Margin: Bicrenated. Texture: Upper surface is slightly velvety. Size of leaf: 79 mm wide, 50 mm long. Color of upper surface: Medium-green, approximately RHS 137 C. Color of lower surface: Near RHS 137 D. Color of zonation: Strong, brown, about RHS 200 B. Size of petioles: 50–60 mm in length, 3 mm in diameter. Color of petioles: RHS 143 C.

*General appearance and form.*—Internode length: 5–10 mm. Branching pattern: 8.2 branches. Plant size: 19 cm high as measured from the base of the stem/soil surface to the surface of the foliage canopy (without inflorescence) and 32 cm wide.

Disease/pest resistance/susceptibility: None observed to date.

I claim:

1. A new and distinct cultivar of geranium plant named 'Fisorange', as described and illustrated.

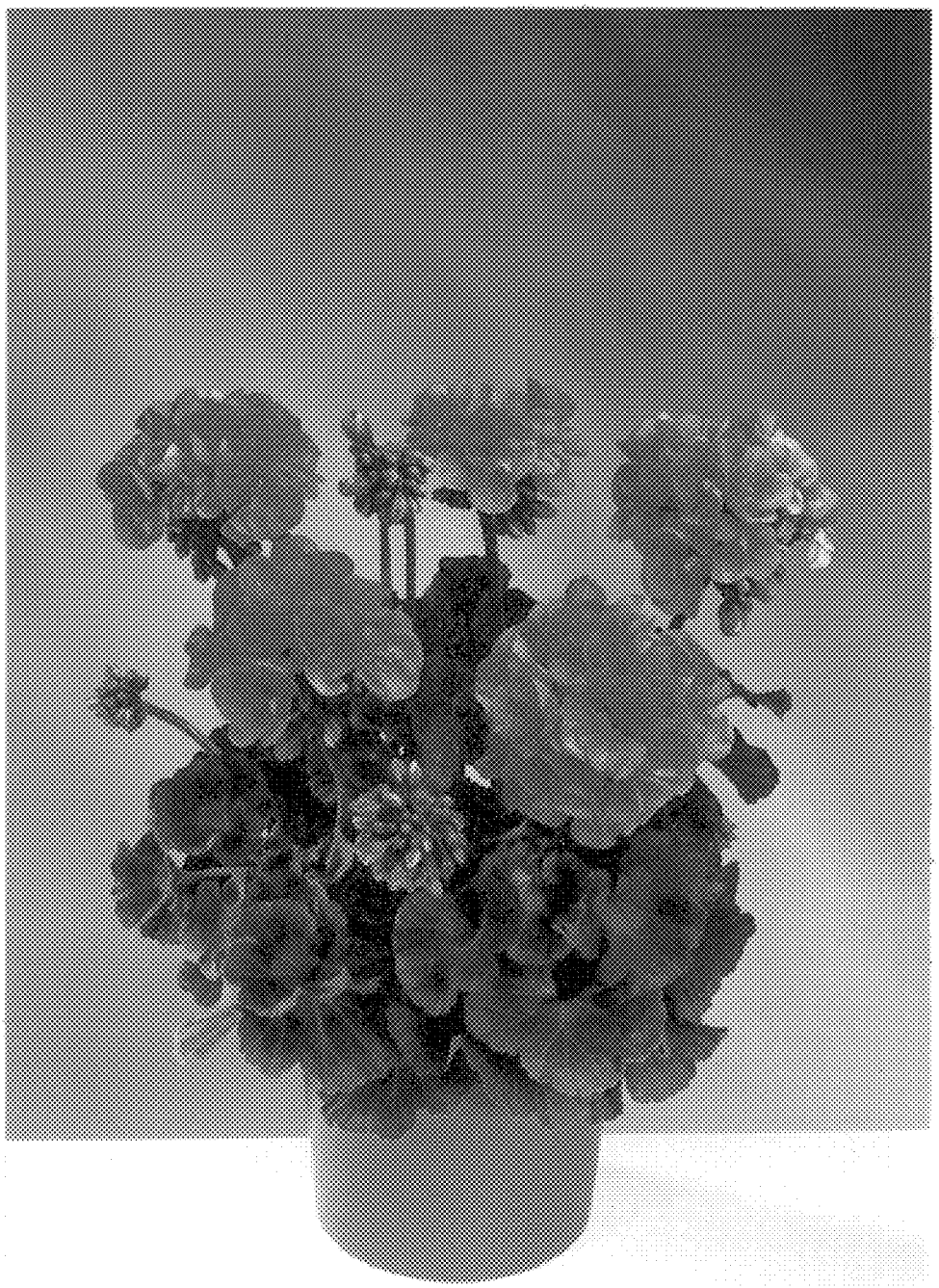

* * * * *